United States Patent
Lau et al.

[11] Patent Number: 5,367,546
[45] Date of Patent: Nov. 22, 1994

[54] FLUID SAMPLING SYSTEM FOR A NUCLEAR REACTOR

[75] Inventors: Louis K. Lau; Naum I. Alper, both of Monroeville, Pa.

[73] Assignee: Westinghouse Electric Corporation, Pittsburgh, Pa.

[21] Appl. No.: 81,753

[22] Filed: Jun. 23, 1993

[51] Int. Cl.⁵ .............................................. G21C 3/56
[52] U.S. Cl. ..................................... 376/392; 376/293; 376/310
[58] Field of Search ............... 376/310, 392, 293, 316, 376/407, 260; 417/158

[56] References Cited

U.S. PATENT DOCUMENTS

| | | | |
|---|---|---|---|
| 3,657,920 | 4/1972 | Teel et al. | 73/28 |
| 3,938,367 | 2/1976 | Fletcher et al. | 73/28 |
| 4,442,720 | 4/1984 | Apley et al. | 73/863.31 |
| 4,493,792 | 1/1985 | Graf, Jr. | 252/627 |
| 4,674,343 | 6/1987 | Larson | 73/864.35 |

*Primary Examiner*—Donald P. Walsh
*Assistant Examiner*—Meena Chelliah

[57] ABSTRACT

A system of extracting fluid samples, either liquid or gas, from the interior of a nuclear reactor containment utilizes a jet pump. To extract the sample fluid, a non-radioactive motive fluid is forced through the inlet and discharge ports of a jet pump located outside the containment, creating a suction that draws the sample fluid from the containment through a sample conduit connected to the pump suction port. The mixture of motive fluid and sample fluid is discharged through a return conduit to the interior of the containment. The jet pump and means for removing a portion of the sample fluid from the sample conduit can be located in a shielded sample grab station located next to the containment. A non-nuclear grade active pump can be located outside the grab sampling station and the containment to pump the nonradioactive motive fluid through the jet pump.

7 Claims, 1 Drawing Sheet

FLUID SAMPLING SYSTEM FOR A NUCLEAR REACTOR

GOVERNMENT CONTRACT

The government of the United States of America has rights in this invention pursuant to contract number DE-AC03-90SF18495 awarded by the Department of Energy.

BACKGROUND OF THE INVENTION

This invention relates to fluid sampling systems for nuclear reactor facilities, and, in particular, systems for extracting liquid and gas samples from selected locations inside nuclear reactor containments.

Nuclear reactors used for power generation are generally surrounded by a concrete or steel enclosure, or containment, that provides shielding in case of an accident that releases radioactive materials. The operating room and other support facilities are located outside the containment such that plant personnel do not normally have to enter the containment. During normal operation, during refueling and after an accident it is desirable to be able to remove samples of fluids, both liquid and gas, from various locations inside the containment to measure radiation levels and perform other types of analysis.

The fluids extracted from the containment are generally pumped through stainless steel plumbing that passes through a shielded sample room located adjacent the containment. Small samples can be removed from the sample room for remote analysis in a laboratory, and the flowing liquids and gases can be continuously monitored in the sample room by measurement instruments having remote displays in the control room. Excess fluids not removed from the sample room are then exhausted to the interior of the containment.

Because the fluids extracted from the containment can be highly radioactive, especially in a post-accident situation, the pumps traditionally used are expensive, nuclear grade active pumps. The pumps; need regular maintenance, therefore, there is redundancy included to allow continuous operation of the sampling system, adding further expense. Additionally, the pumps can themselves become activated by the radioactive materials flowing through them. This can make maintenance of the pumps difficult and hazardous to personnel, and also creates a waste disposal problem.

SUMMARY OF THE INVENTION

It is an object of this invention to provide a method of extracting fluid samples from a nuclear reactor containment without the use of nuclear grade active pumps.

It is another object of this invention to provide a system of extracting fluid samples from a nuclear reactor containment that is less expensive than traditional methods.

These objects and others which will become more readily apparent are realized in accordance with this invention. According to the invention, the pumping of fluids, both in liquid and gaseous states, from a nuclear reactor containment is accomplished with jet pumps. Jet pumps have no moving parts. Their construction is essentially that of a three port manifold having inlet, suction and discharge ports. When used to pump liquids they are called "eductor" pumps; for gases they are called "ejector" pumps. Physically they are identical. In either case, a motive fluid (liquid or gas, depending upon whether the fluid to be pumped is liquid or gas) is forced through the inlet port and discharged through the discharge port. The motion of the motive fluid creates a suction at the suction port, drawing in the fluid that is to be pumped into the jet pump where it mixes with the motive fluid before discharge.

According to this invention, a method of extracting a sample fluid, either liquid or gas, from the interior of a nuclear reactor containment is provided by the steps of providing a jet pump at a location outside the containment; providing a sample fluid conduit, or piping, for drawing the sample fluid from the interior of the containment to the suction port of the jet pump; providing a return fluid conduit from the discharge port of the jet pump to the interior of the containment; generating a flow of a non-radioactive motive fluid (liquid for a liquid sample fluid; gas for a gas sample fluid) into the inlet port of the jet pump and out the discharge port; creating a suction, or low pressure condition, at the suction port with the flow of motive fluid; drawing the sample fluid with the suction through the sample fluid conduit from the containment to the suction port; and discharging the mixture of the sample fluid and the motive fluid through the return fluid conduit into the containment.

According to another aspect of this invention, a step of enclosing the jet pump and a portion of the sample fluid conduit in a radiation shielded enclosure, or grab sampling station, that is located in a sample room outside the containment, is performed prior to the step of creating the suction. This provides radiation shielding to protect personnel and the environment from the radioactive fluids that flow through that part of the system located outside the containment. The further step of removing a portion of the sample fluid from a sampling section of the sample fluid conduit, at a location from within the grab sampling station, can then be done safely after drawing the sample fluid into the conduit. Diluting the sample fluid with a nonradioactive fluid prior to removing it from the sample section allows the sampling of highly radioactive fluids.

Also according to the invention, the motive fluid is provided from a source outside the grab sampling station. This feature allows the use of non-nuclear grade pumps for any active pumps used in the system. The active pumps are not exposed to any radiation, and so can be serviced at any time without taking precautions normally used when handling hazardous, radioactive materials.

BRIEF DESCRIPTION OF THE DRAWING

The drawing is a plumbing schematic of apparatus used with this invention.

DETAILED DESCRIPTION OF THE INVENTION

Figure 1:
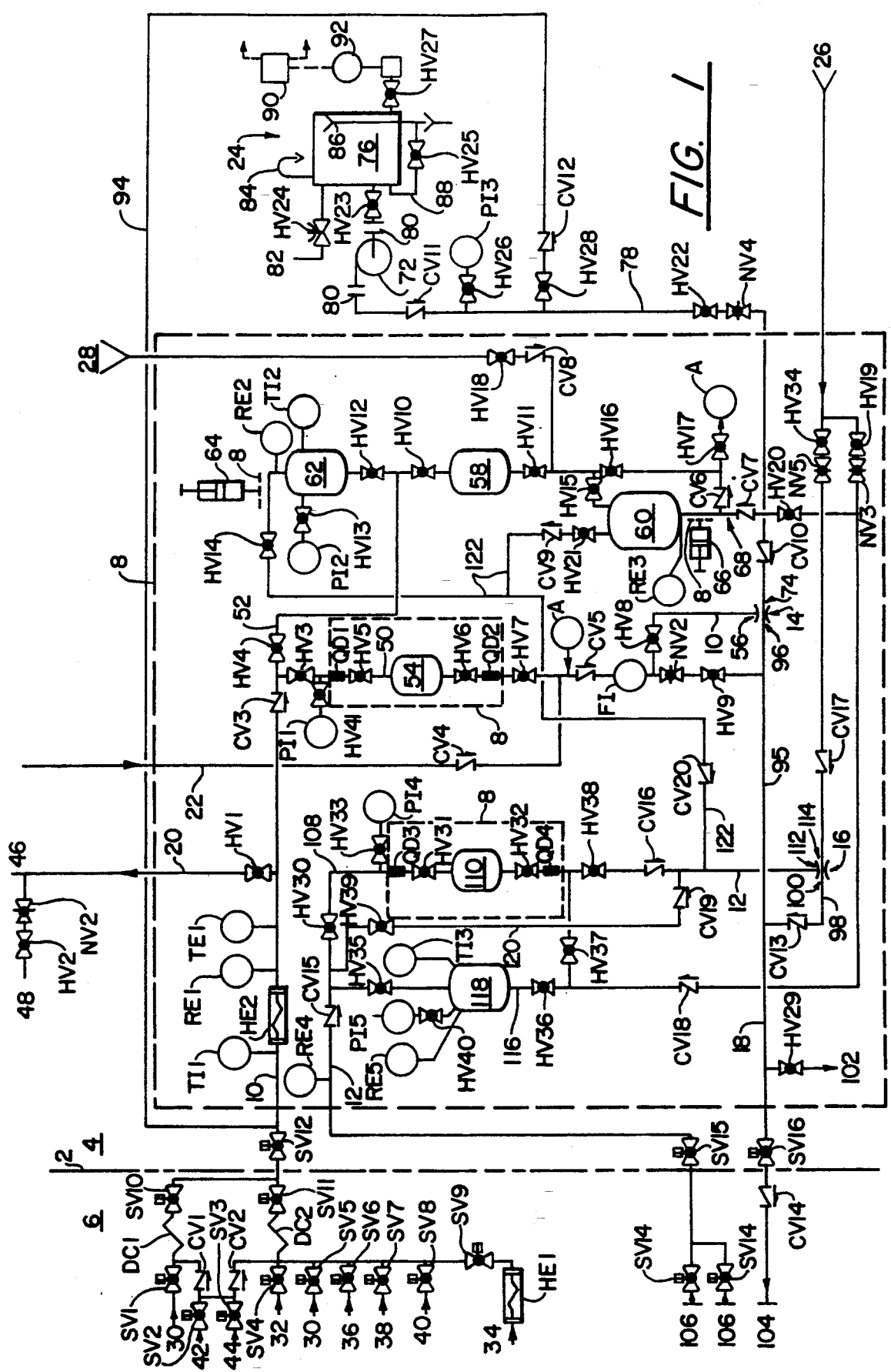

The fluid extraction system of this invention, while being designed for use in the nuclear power industry, has broader applications for facilities that handle hazardous or corrosive fluids. Active pumps are entirely separated from the hazardous fluids, allowing the use of less expensive active pumps, not requiring special seals or shielding, to pump the motive fluids. Maintenance on the active pumps can be carried out without exposing personnel to the hazardous materials. In fact, active pumps are not even needed to extract sample fluids—it is only necessary to have a source of pressurized motive fluid. For example, tap water could be used to operate an eductor pump to extract liquids, and a cylinder of pressurized $N_2$ gas could be used to operate an ejector pump to extract gases.

Referring to the drawing, a nuclear reactor containment 2 divides and protects the exterior environment 4 from a nuclear reactor (not shown) that is located in the interior 6 of the containment. A grab sampling station 8 located inside a sample room (not shown) positioned close to the exterior wall of the containment 2 provides a shielded enclosure for removing samples of fluids, both liquid and gaseous, for analysis. A sample liquid conduit 10 and a sample gas conduit 12 carry sample fluids from the interior of the containment 6 into the grab sampling station 8 where they are drawn by an eductor pump 14 and an ejector pump respectively. A common return fluid conduit 18 discharges liquid and gas contaminants back into the containment from the jet pumps. Other conduits 20, 22, connect the sample fluid conduits to and from equipment in laboratories (not shown) outside the grab sampling station 8. Outside the grab sampling station are liquid 24 and gaseous 26 sources of nonradioactive motive fluids. A source of a diluting liquid 28, preferably deionized water, is also provided from outside the grab sampling station. The grab sampling station 8 also has a door (not shown) so that plant personnel can enter to perform maintenance within the station if necessary. According to a preferred embodiment of the invention, the grab sampling station 8 is made of stainless steel and is about six feet wide by eight feet long, having sufficient height for a person to comfortably work inside.

Small samples of liquids and gases, called grab samples, are taken from detachable sample bottles or from syringes located on the exterior wall of the grab sampling station 8 and connecting to the sampling section within the station. All valves located within the grab sampling station 8 have stems extending outside the station to exterior handles so that an operator can safely control the flow of sample fluids without entering the station. Pressure, temperature, radiation and flow sensors within the grab sampling station provide visual and recorded indications of those variables to locations outside the station.

Turning now to the specific details of a preferred embodiment of the liquid sampling system, the sample liquid conduit 10 is fed from several sources within the containment 6. Liquid samples are drawn from the reactor coolant system (RCS) hot leg 30, the RCS pressurizer liquid space 32 and the RCS pressurizer vapor space 34 lines. The pressurizer vapor is condensed by a heat exchanger HE1 prior to entering the sample liquid conduit 10 and leaving the containment. Other sources of sample liquids include the passive safety injection system (PXS) accumulator 36, or tank, the PXS core makeup tank 38, and the chemical and volume control system (CVS) 40 that maintain the chemistry and volume of the reactor coolant. Fluids pumped from the waste liquid sump (WLS) 42 and demineralized water 44 from inside the containment 6 can be added to any of the foregoing sample liquid sources. Delay coils DC1, DC2, check valves CV1, CV2, and automated solenoid valves SV1–SV11 control the flow of sample liquids into the sample liquid conduit 10 prior to exiting the containment. Another solenoid valve SV12 can be used to shut off flow between the containment 2 and the sample room (not shown).

Within the grab sampling station 8, a temperature indicator TI1 provides an indication of the sample liquid temperature as it enters the room. A heat exchanger HE2 cools the high temperature fluid in the sample liquid conduit 10 to a lower and workable temperature. Downstream from the heat exchanger HE2, a radiation sensor RE1 and a temperature sensor TE1 provide recorded and visual readings of those parameters to a location outside the grab sampling station. A liquid conduit 20 branches from the sample liquid conduit 10 and leads to lab equipment 46 and a chemical sink hood 48 in a laboratory (not shown) outside the grab sampling station 8. Hand operated valves HV1, HV2 and needle valve NV1 control the flow of liquid to the laboratory. The liquid is then returned from the laboratory via conduit 22 back to conduit 50. A stop check valve CV4 provides unidirectional flow control. A check valve CV3 maintains fluid flow in a single direction in the sample liquid conduit 10.

At this point the sample liquid conduit 10 branches to two different conduit lines 50, 52, the flow through each branch being controlled by hand operated valves HV3, HV4, respectively. The first branch 50 has a sampling bottle 54 having a predetermined capacity, preferably a capacity of about 100 ml. The sampling bottle 54 can be closed off from the line by hand operated valves HV5, HV6 and removed from the line by disconnecting quick disconnect fittings QD1, QD2 after the sampling bottle 54 has been isolated. As noted above, the sampling bottle can be located outside but close to the grab sampling station 8, as indicated in the drawing. In that case, valves HV5, HV6 and quick disconnect fittings QD1, QD2 are also located just outside the grab sampling station 8. While filling the sampling bottle 54, the pressure in the first line can be monitored with a pressure indicator PI1. Further downstream along the first branch is another hand operated valve HV7 and a fluid conduit that returns liquids from the laboratory outside the grab sampling station 8.

Just downstream from fluid conduit 22 and upstream from check valve CVS, the second branch 52 rejoins the first branch 50 at point A. Flow indicator FI allows monitoring of the flow rate in the sample liquid conduit branch 50, or the lab return conduit 22, depending upon which conduit is in use. Hand valve EV8 controls flow of sample liquid to the suction port 56 of the eductor pump 14. Needle valve NV2 and hand operated valve EV9 control flow to the return fluid conduit 18. Needle valve HV2 is used to control the flow to a desired rate and to reduce the normally high pressure sample fluid to a lower pressure. Either valve HV8 or valve HV9 is closed to control flow to only one path.

The second branch 52 of the sample liquid conduit 10, before rejoining the first branch 50, leads to a sampling chamber 58 and a dilution chamber 60 as depicted in the drawing. The sampling chamber is used in conjunction with an expansion cylinder 62, located at an elevation above the sampling chamber 58, and with the ejector pump 16 for extracting gases that are dissolved in the sample liquid by a process that is explained infra. Hand operated valves HV10, HV11 can be used to isolate the sampling chamber and hand operated valves HV12–HV14 can be used to isolate the expansion cylinder 62 from the sampling chamber 58, the ejector pump 16 and a vacuum protected pressure indicator PI2. An arrangement is provided for removing a gas sample from the expansion cylinder 62, preferably a shielded syringe 64. The expansion chamber also has a radiation sensor RE2 that can provide a readout at a remote location, such as the control room (not shown), and a temperature indicator TI2.

Downstream from the sampling chamber 58 and the hand operated valve HV11 is the dilution chamber 60. The flow of sample liquid into and out of the dilution chamber is controlled by hand operated valves HV15-HV17 and check valves CV6, CV7. A diluting liquid, preferably deionized water, can be added to the dilution chamber 60 from source 28. This diluting volume is predetermined to dilute a known sample fluid volume from the liquid sampling chamber 58, the predetermined diluting volume being the volume within the liquid line between hand operated valves HV11, HV15, HV16 and CV8. The flow of diluting liquid into that volume is controlled by hand operated valve HV18 and check valve CV8. A radiation sensor RE3 provides a recorded reading of the radiation from the contents of the dilution chamber 60. Means 66 for removing a small quantity of a diluted liquid sample from the dilution chamber 60 can be a shielded syringe extending outside the grab sampling station 8, as depicted in the drawing. An arrangement 68 for mixing the contents of the dilution chamber 60 utilizes nonradioactive $N_2$ gas that is bubbled up through the chamber contents. The gas is supplied from the same source as for the nonradioactive motive gas 26. Hand operated valves HV19-HV21, needle valve NV3 and check valves CV7 and CV9 control the flow of gas into and out of the dilution chamber 60.

The nonradioactive motive fluid, preferably deionized water, is pumped by a non-nuclear grade active pump 72 to the inlet 74 of the eductor pump 14 from a tank 76 located outside the grab sampling station 8 and the containment 2 via a nonradioactive motive liquid conduit 78. The pump 72 can be located in the sample room, if desired. The flow to the inlet 74 is controlled by hand operated valves HV22, HV23, check valves CV10, CV11 and needle valve NV5, as depicted in the drawing. The active pump can be safely and easily removed for repair or replacement by closing valves HV22, HV23 and disconnecting flanges 80. The deionized water is pumped into the tank from a separate source 82 (that can be the same as source 44) through a line having control valve HV24. The tank 76 has a vent 84, a passive overflow drain 86, and a bottom drain 88 controlled by valve HV25. A pressure sensor PI3 indicates the pressure within the motive liquid conduit 78. The pressure sensor PI3 can be valved off by valve HV26. A level indication alarm 90 in a remote operating room (not shown) signals personnel when the contents of the tank 76 are low. The alarm 90 is controlled by a level indication switch 92 that can be valved off from the tank by valve HV27. A liquid flush conduit 94 brings nonradioactive liquid from the tank 76 to the sample liquid conduit at a point between the containment 2 and the grab sampling station 8, providing means for flushing the system components outside the containment 4 with uncontaminated water, even when deionized water 44 from inside the containment 6 is not available. The flow from the pump 72 is controlled by a hand operated valve HV28 and a check valve CV12.

The return fluid conduit 18 is fed from two branches, a liquid return conduit 94 that connects to the discharge port 96 of the eductor pump 14, and a gas return conduit 98 that connects to the discharge port 100 of the ejector pump 16. A check valve CV13 prevents liquids from backing into the ejector pump 16. The fluids can be discharged to either the radiated WLS borated effluent holdup tank 102 (not shown) or to the recirculation containment sump 104 in the containment 6, or to some other safe repository. The flow to the former is controlled by a hand operated valve HV29, and the flow to the latter by a solenoid valve SV16 and a check valve CV14.

The plumbing arrangement for the extraction of a sample gas from within the containment 6 is similarly straightforward. Sample gases are extracted from sample locations 106 inside the containment 6 via a sample gas conduit 12. Automated solenoid valves SV14 are used to control the flow into the sample gas conduit 12 inside the containment 6. Another automated solenoid valve SV15 is provided between the grab sampling station 8 and the containment 2. Inside the grab sampling station 8, a radiation sensor RE4 provides a means for monitoring and recording the radiation in the sample gas conduit 12. The sample gas conduit 12 has three main branches inside the grab sampling station 8. The flow to the branches is maintained unidirectional by a check valve CV15.

The first branch 108, the flow to which is controlled by a hand operated valve HV30, leads to a gas sampling bottle 110. The sampling bottle can be isolated by hand operated valves HV31, HV32. Once isolated, the sampling bottle 110 can be removed from the first branch 108 by releasing quick-disconnect fittings QD3, QD4, and then removed from the grab sampling station 8. As with the sampling bottle 54 for liquid samples, the sampling bottle 110 for gases, valves HV31, HV32 and fittings QD3, QD4 are preferably located just outside the grab sampling station S. A pressure sensor PI4, that can be isolated from the first branch 108 by hand operated valve HV33, gives an indication of the pressure in that line. Downstream from the sample bottle 110 the first branch 108 feeds into the ejector pump suction port 112. Flow of sample gases to the ejector pump is maintained in one direction by a check valve CV16. The nonradioactive motive gas from source 26, preferably $N_2$ gas from a regulated cylinder (not shown), located outside the grab sampling station 8 is fed into the ejector pump inlet 114 under pressure. The flow to the ejector pump 16 is further regulated in the grab sampling station 8 by a hand operated valve HV34, a needle valve NV5, and a check valve CV17. The needle valve NV5 controls the pressure in the line.

The second branch 116 for the sample gases leads to a gas diluting chamber 118 before rejoining the first branch 108 downstream from the quick-disconnect fitting QD4 and upstream from valve HV38. The gas dilution chamber can be isolated by valves HV35, HV36. A nonradioactive diluting gas, preferably $N_2$ from the motive gas source 26, can be added to the gas dilution chamber 118 to dilute the sample gas extracted from within the containment 6. The diluting gas is introduced through valves HV19, NV3 and HV36 while valve HV37 is closed. Backflow of radioactive sample gas is prevented by check valve CV18. The radiation level, the pressure and the temperature of the contents of the gas dilution chamber are monitored with sensors RE5, PI5 and TI3, respectively. The radiation level can be advantageously monitored and recorded in a remote location, e.g. the control room (not shown).

The third branch 120 is a bypass of the other branches 108, 116. Flow through the third branch 120 is controlled by a hand operated valve HV39 and a check valve CV19 before it rejoins the sample gas conduit 12 upstream from the ejector pump 16. Another gas conduit 122 also connects the expansion cylinder 62 and the dilution chamber 60 to the gas sample conduit 12 upstream from the ejector pump 16, the flow being regulated by hand operated valves HV14, HV21 and check valves CV9, CV20.

Operation of the system to extract sample liquid and gas fluids from the containment is simple. For example, an operator may want to fill the sampling bottle 54 with sample liquid from the RCS hot leg 30 for removal from the grab sampling station 8. If the system already has some leftover sample fluids in it from a prior extraction operation, the operator may flush the system by flowing nonradioactive water from tank 76 through the grab sampling station 8 plumbing via conduit 94 while keeping valve SV12 closed. This operation can be performed while the motive fluid is flowing through the eductor pump 14. The section of sample liquid conduit 10 inside the containment may be flushed with deionized water from source 44. The nonradioactive water used for flushing can also serve to prime the sample liquid conduit 10, if necessary. Valves HV1, HV4, HV9, HV17, HV28, HV29 and NV2 are then shut while valves HV3, HV5–HV8, HV22, NV4 and SV16 are kept open. Valves SV1, SV10 and SV12 are then opened to allow the liquid from the RCS hot leg 30 to be drawn from the inside of the containment 6 by the suction of the eductor pump 14 through sample fluid conduit 10 into the sampling bottle 54. Once the bottle 54 filled with the sample liquid, it can be isolated by closing valves HV3 and HV5–HV7, then removed from the conduit 10 by disconnecting quick disconnect fittings QD1 and QD2. During the operation, excess fluids are discharged into the recirculation containment sump 104.

After an accident it may be necessary to extract highly radioactive samples from the containment. Dilution of these samples with a nonradioactive diluting fluid would then be desirable. To extract a small sample of a diluted liquid, the operator makes sure that the dilution chamber 60 is flushed and drained of liquids, purged with nonradioactive $N_2$ gas, and then isolated by closing valves HV15, HV20 and HV21. The first branch 50 of the sample liquid conduit is closed off by closing valves HV3 and HV7. Suction from the eductor pump 14 is maintained and flow through the second branch 52 is limited to a path through the sampling chamber 58 by closing valves HV9, HV12 and HV18 while keeping valves HV4, HV8, HV10–HV11 and HV17 open. By closing valves HV16 and then HV11, a known volume of highly radioactive sample liquid can be isolated in the second branch conduit section defined by the volume contained between valves HV11, HV15, HV16 and CV8. The contents of the sampling chamber 58 can be added to this volume, if desired, by closing HV10 instead of HV11. The known volume can then be drained by gravity into the dilution chamber by opening valve HV15 after closing valve HV17. A small sample can be extracted immediately with a shielded syringe 66 that extends outside the grab sampling station 8, or the contents of the dilution chamber 60 can be diluted first with a predetermined volume of nonradioactive, deionized water from source 28 from outside the grab sampling station 8. Nonradioactive, pressurized $N_2$ gas can be bubbled through the contents of the dilution chamber 60 to mix them. The pressurized gas is introduced into the bottom of the dilution chamber 60 via valve HV20 and flows out from the top of the dilution chamber by the suction 112 of the ejector pump 16 through valve HV21 and via conduit 122. Check valve CV7 prevents backflow of the liquid contents of the dilution chamber 60. Keeping valves HV16, HV17 closed assures that the $N_2$ gas flows through the dilution chamber 60 only. Once diluted, the sample liquid can be more safely handled and withdrawn using the shielded syringe Extraction of sample gases is also simple. After purging the sample gas conduit with nonradioactive $N_2$ gas from a pressurized and regulated tank 26 located outside the grab sampling station 8 and creating a suction in sample gas conduit 12 by flowing nonradioactive motive gas through the ejector pump 16, valves HV29, HV35, HV37 and HV39 are closed, while valves HV30–HV32, HV38 and HV14–HV15 are opened. This allows sample gas from locations 106 inside the containment 6 to be drawn by suction from the ejector pump 16 through sample gas conduit 12 and branch 108 having the sampling bottle 110. Waste gases can be discharged back to the interior of the containment 6 through conduit 18. To remove a sample, the sample bottle 110 is first isolated by closing valves HV30–HV33 and HV38. The bottle may then be disconnected from the branch 108 by disconnecting quick disconnect fittings QD3 and QD4. Since the gas sample bottle 110, valves HV31, HV32 and quick disconnect fittings QD3, QD4 are located on the outside wall of the grab sampling station 8, the operator need not enter the station.

A highly radioactive gas sample can be directed to the gas diluting chamber 118 by first evacuating and then closing off sample gas conduit branches 108 and 120 (closing valves HV30, HV32 and HV39). Highly radioactive sample gas can then flow through branch 116 by opening valves HV35–HV38 and SV14 and SV15 after establishing a suction in the sample gas conduit 12 with the ejector pump 16. Closing valves HV37 and HV35 isolates the sample in the gas dilution chamber 118. The pressure, temperature and radiation levels can be monitored with sensors PI5, TI3 and RE5. Nonradioactive $N_2$ gas can be introduced into the gas sampling chamber 118 by opening valves HV19 and NV3 and closing HV34. Monitoring change in temperature and pressure provides an indication of the degree of dilution. A portion of the contents of the chamber 118 can be removed by first closing valve HV38 and then opening up valves HV37, HV31–HV33, allowing the previously evacuated sample bottle 110 to fill with the diluted gas sample. The sample bottle 110 can then be removed by the method described above.

An operator can also use this invention to extract from a containment a liquid sample that contains dissolved gases, and then extract the gases from the liquid. First, the sample liquid conduit 10 and the sample gas conduit 12 are preferable flushed and purged by the method described above. The liquid sampling chamber 58 is then at least partially filled with the sample liquid containing the dissolved sample gases. Valves HV4, HV11 and HV12 are closed, isolating the sample liquid in the sampling chamber 58 from the rest of the system. Making sure that the expansion cylinder 62 is first evacuated to a pressure below atmospheric pressure by the suction of the ejector pump 16 via conduit 122, then valve HV12 is opened and valve HV14 is closed. This allows the dissolved gases in the liquid in the sampling chamber 58 to be drawn out of solution by the reduced pressure over the sample liquid surface. The pressure, temperature and radiation of the gases in the expansion chamber can be monitored by pressure sensor PI2, temperature sensor TI2 and radiation sensor RE2. A small sample of the gas drawn out of solution can then be removed using shielded syringe 64, located outside the grab sampling station 8, if desired.

Although the preferred embodiment of the invention described above is an interconnected arrangement of plumbing tubes, valves and sensors to provide versatility for operation of a nuclear reactor facility, such complexity of design is not at the core of the invention. The basic system is simply a jet pump located outside the containment, preferably in a separate shielded enclosure, drawing fluids from the containment by use of a flow of a nonradioactive motive fluid generated from outside the containment and the shielded enclosure. The jet pump has no moving parts or seals, and is therefore virtually maintenance free. Any active pumps are located outside the shielded enclosure and are never exposed to the hazardous sample fluids, allowing the use of equipment without special seals or shielding. Thus, both capital costs and maintenance costs can be reduced.

It is understood that various modifications of these systems may occur to those skilled in the art and it is intended that this invention be limited only by the scope of the claims.

We claim:

1. A method of extracting a sample gas from the interior of a nuclear reactor containment, the sample gas being in solution in a sample liquid located inside the containment, comprising the steps of:
   providing an eductor pump outside the containment;
   providing an ejector pump outside the containment;
   providing a sample liquid conduit from the containment to a suction port of the eductor pump, the sample liquid conduit being characterized by a liquid sampling section comprising a sampling chamber, first liquid valve means for isolating the sampling chamber from the containment and second liquid valve means for isolating the sampling chamber from the eductor pump, the liquid sampling section being located outside the containment;
   providing a return liquid conduit from a discharge port of the eductor pump to the interior of the containment;
   providing a sample gas conduit from the sampling chamber to a suction port of the ejector pump, the sample gas conduit being characterized by a gas sampling section comprising an expansion cylinder located at an elevation above the sampling chamber and having a sample gas extraction port, first gas valve means for isolating the expansion cylinder from the sampling chamber and second gas valve means for isolating the expansion cylinder from the ejector pump, the gas sampling section being located outside the containment;
   providing a return gas conduit connecting a discharge port of the ejector pump to the interior of the containment;
   generating a flow of a non-radioactive motive liquid into an inlet port of the eductor pump and out the discharge port of the eductor pump;
   creating a first suction in the sample liquid conduit with the flow of motive liquid;
   opening the first and second liquid valve means;
   drawing the sample liquid into the sampling chamber with the first suction;
   closing the second liquid valve means to isolate the sampling chamber from the eductor pump;
   closing the first liquid valve means to isolate the sampling chamber from containment;
   closing the first gas valve means;
   generating a flow of a non-radioactive motive gas into an inlet port of the ejector pump and out the discharge port of the ejector pump;
   creating a second suction in the sample gas conduit with the flow of motive gas;
   evacuating the expansion cylinder by opening the second gas valve means;
   closing the second gas valve means; and
   opening the first gas valve means.

2. The method of claim 1, further comprising the step of enclosing the eductor pump, the ejector pump, the liquid sampling section and the gas sampling section in a radiation shielded enclosure before drawing the sample liquid into the sampling chamber.

3. The method of claim 2, wherein the step of generating a flow of a non-radioactive motive liquid is characterized in that the flow is generated from a source located outside the shielded enclosure and outside the containment and wherein the step of generating a flow of a non-radioactive motive gas is characterized in that the flow is generated from a source located outside the shielded enclosure and outside the containment.

4. The method of claim 3, further comprising the step of extracting a portion of the contents of the expansion cylinder from the sample gas extraction port after opening the first gas valve means.

5. Apparatus for extracting a sample gas from the interior of a nuclear reactor containment, the sample gas being in solution in a sample liquid located inside the containment, comprising:
   an eductor pump located outside the containment;
   an ejector pump located outside the containment;
   a sample liquid conduit from the containment to a suction port of the eductor pump, the sample liquid conduit being characterized by a liquid sampling section comprising a sampling chamber, first liquid valve means for isolating the sampling chamber from the containment and second liquid valve means for isolating the sampling chamber from the eductor pump, the liquid sampling section being located outside the containment;
   a return liquid conduit from a discharge port of the eductor pump to the interior of the containment;
   a sample gas conduit from the sampling chamber to a suction port of the ejector pump, the sample gas conduit being characterized by a gas sampling section comprising an expansion cylinder located at an elevation above the sampling chamber and having a sample gas extraction port, first gas valve means for isolating the expansion cylinder from the sampling chamber and second gas valve means for isolating the expansion cylinder from the ejector pump, the gas sampling section being located outside the containment;
   a return gas conduit from a discharge port of the ejector pump to the interior of the containment;
   means for generating a flow of a non-radioactive motive liquid into an inlet port of the eductor pump and out the discharge port of the eductor pump; and means for generating a flow of a non-radioactive motive gas into an inlet port of the ejector pump and out the discharge port of the ejector pump.

6. The apparatus of claim 5, further comprising a radiation shielded enclosure located outside the containment and enclosing the eductor pump, the ejector pump, the liquid sampling section and the gas sampling section.

7. The apparatus of claim 6, wherein means for generating a flow of a non-radioactive motive liquid is characterized by a source of pressurized non-radioactive motive liquid located outside the shielded enclosure and outside the containment, and wherein the means for generating a flow of a non-radioactive motive gas is characterized by a source of pressurized non-radioactive motive gas located outside the shielded enclosure and outside the containment.

* * * * *